US00RE35848E

United States Patent [19]

Tanaka

[11] E Patent Number: Re. 35,848

[45] Reissued Date of Patent: Jul. 14, 1998

[54] X-RAY CT SCANNER

[75] Inventor: Shigeru Tanaka, Ootawara, Japan

[73] Assignee: Kabushiki Kaisha Toshiba, Kawasaki, Japan

[21] Appl. No.: 547,153

[22] Filed: Oct. 24, 1995

Related U.S. Patent Documents

Reissue of:

[64] Patent No.: 5,103,469
Issued: Apr. 7, 1992
Appl. No.: 662,995
Filed: Feb. 28, 1991

U.S. Applications:

[63] Continuation of Ser. No. 352,539, May 16, 1989, abandoned.

[30] Foreign Application Priority Data

May 20, 1988 [JP] Japan ..... 63-124493

[51] Int. Cl.[6] ..... A61B 6/00

[52] U.S. Cl. ..... 378/16; 378/20; 378/98.2; 378/205

[58] Field of Search ..... 378/16, 20, 205, 378/98.2, 4, 109, 110, 111, 112, 195, 196, 96, 97, 108

[56] References Cited

U.S. PATENT DOCUMENTS

| | | | |
|---|---|---|---|
| 3,991,314 | 11/1976 | Schmitman et al. | 378/108 |
| 4,032,784 | 6/1977 | Rich | 378/112 |
| 4,260,894 | 4/1981 | Neumann | 378/97 |
| 4,403,337 | 9/1983 | Kleinman | 378/96 |
| 4,595,949 | 6/1986 | Fenster et al. | 378/110 |
| 4,624,007 | 11/1986 | Muranushi | 378/20 |
| 4,649,555 | 3/1987 | Matsubayashi | 378/20 |
| 5,103,469 | 4/1992 | Tanaka | 378/16 |

FOREIGN PATENT DOCUMENTS 52860 3/1986 Japan .

*Primary Examiner*—David P. Porta
*Attorney, Agent, or Firm*—Finnegan, Henderson, Farabow, Garrett & Dunner, L.L.P.

[57] ABSTRACT

An X-ray CT scanner having an X-ray tube for emitting X-rays to a subject under examination and an X-ray detector for detecting X-rays emitted by the X-ray tube and passed through the subject. The X-ray CT scanner photographs a scanogram of the subject first and then photographs slice images of the subject in slice positions set on the scanogram. The X-ray CT scanner includes a scan condition setter for determining optimum scan conditions including optimum X-ray tube current or the optimum X-ray tube voltage for each of slice position and optimum shifted positions of the X-ray tube and X-ray detector in the case of an X-ray CT scanner with a shift mechanism for photographing the slice images on the basis of photographic data of the scanogram and a scan controller for controlling the execution of photographing of the slice images in accordance with the scan conditions determined by the scan condition setter.

84 Claims, 3 Drawing Sheets

X-RAY CT SCANNER

Matter enclosed in heavy brackets [ ] appears in the original patent but forms no part of this reissue specification; matter printed in italics indicates the additions made by reissue.

This application is a continuation of application Ser. No. 07/352,539 filed May 16, 1989 now abandoned.

BACKGROUND OF THE INVENTION

1. Field of the Invention

The present invention relates to an X-ray CT (computed tomography) scanner for photographing a scanogram and slice image of a subject under examination.

2. Description of the Related Art

X-ray CT scanners generally make tomograms (here called slice images) of a plurality of parallel slices of a subject under examination which are normal to the body axis of the subject. In this case, a scanogram of the subject is taken previously so as to locate the slices. That is, a scanogram which is substantially the same as a usual X-ray photograph is obtained by irradiating the subject with X-rays in synchronization with the movement of the top board of an examination couch on which the subject lies while the top board is moved through between an X-ray tube and an X-ray detector which are fixed in their respective positions. A plurality of lines representing a plurality of positions (slice positions) having a predetermined slice pitch and allowing slice images to be taken are superimposed on the scanogram on a CRT display of the X-ray CT scanner. An operator determines the position of each slice in accordance with the image on the CRT display and then enters a number corresponding to the line on the CRT display through a keyboard. The top board of the examination couch is automatically moved so that the slice to be taken of the subject is positioned directly below the X-ray tube and afterward a slice image is photographed by scanning the X-ray tube around the subject. This operation is referred to as the auto index scan.

In the auto index scan, a current of the X-ray tube (referred to as a tube current hereinafter) at the time of photographing of a slice image can be selected by switches or the like provided on a console panel. This is to secure the optimum exposure of X-rays for a portion to be photographed. Depending upon X-ray CT scanners, the X-ray tube and the X-ray detector can be shifted along a line connecting the centers thereof, and moreover the shift amount can be selected according to the size of a subject under examination. Furthermore, the tube voltage as well as the tube current may be selected.

With the conventional X-ray CT scanner, however, the so-called scan conditions, such as the tube current, the shift amount, and the tube voltage, are set empirically by an operator. Thus, an operator having little experience has to set the scan conditions on a trial and error basis. This makes the optimum setting of scan conditions very difficult. Even a well experienced operator the optimum scan conditions for each of slices. For this reason, a burden imposed on the operator in setting the scan conditions is heavy.

SUMMARY OF THE INVENTION

It is accordingly an object of the present invention to provide an X-ray CT scanner which alleviates the burden imposed on an operator with an automated system for setting scan conditions.

To achieve the object, an X-ray CT scanner according to an aspect of the present invention comprises means for emitting X-rays to a subject under examination; means for detecting X-rays emitted by the X-ray emitting means and passed through the subject; scanogram means, coupled to the emitting means and the detecting means, including means for moving the X-ray emitting means with the detecting means along the subject and means for photographing a scanogram of the subject; determining means, coupled to the scanogram means, for determining a scan condition from image information for a predetermined position in the scanogram; means, coupled to the determining means, for scanning a portion of the subject corresponding to the predetermined position in the scanogram in accordance with the scan condition determined by the determining means including means for rotating the X-ray emitting means and the detecting means around the subject; and means for reconstructing a slice image of the portion of the subject based on the output from the detecting means during scanning by the scanning means.

The scanogram is photographed by directing X-rays to a subject under examination. By using the resultant photographic data of the scanogram, therefore, it is possible to determine the optimum scan conditions for photographing slice images. According to such automated setting of scan conditions, it becomes possible to set the optimum scan conditions for each of slices irrespective of presence or absence of operator's experience in setting scan conditions, thus alleviating the burden imposed on the operator considerably.

DETAILED DESCRIPTION OF THE PREFERRED EMBODIMENTS

Figure 1:
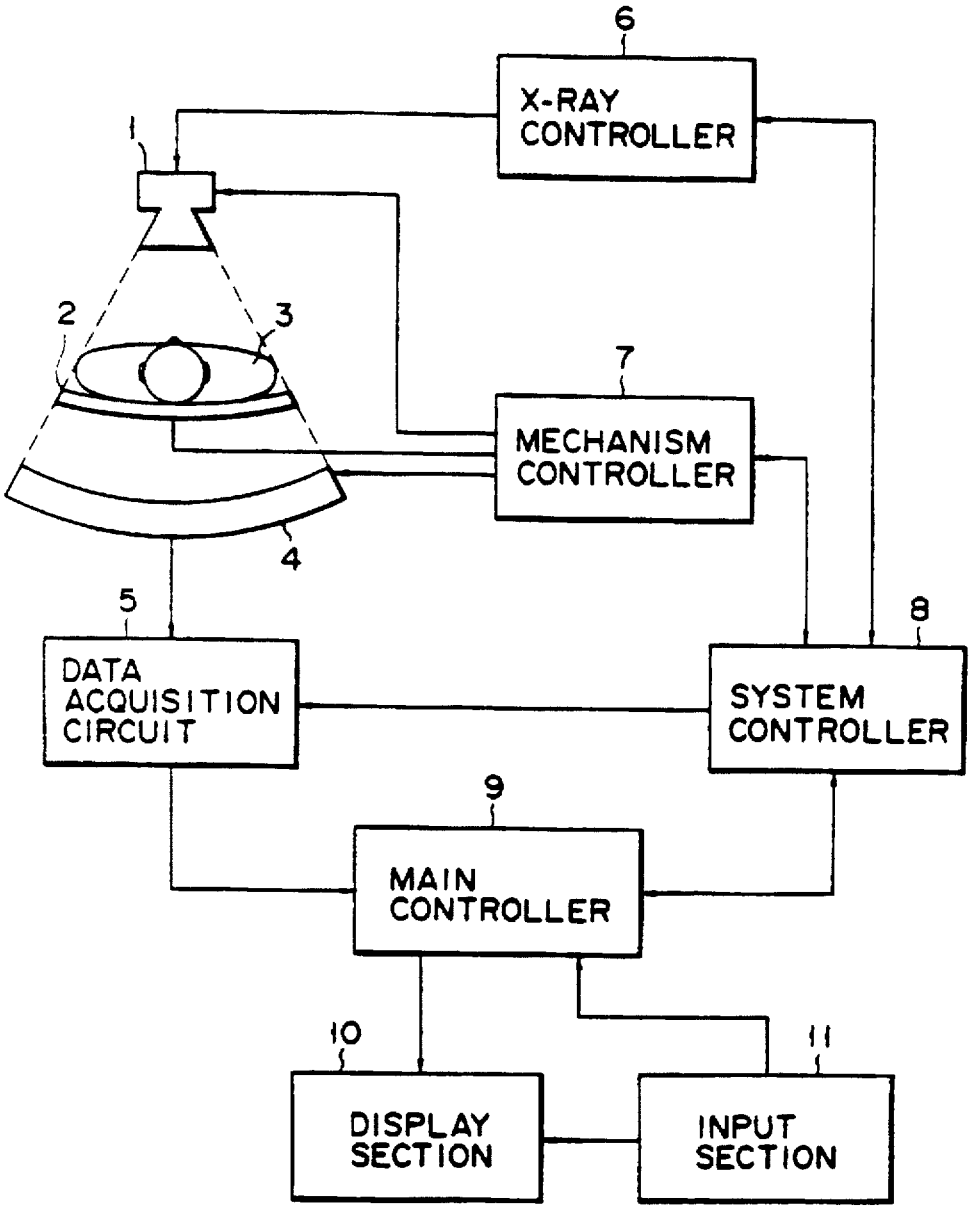
FIG. 1 is a block diagram of an X-ray CT scanner embodying the present invention.

Referring now to FIG. 1, an X-ray tube 1 and an X-ray detector 4 are installed in a gantry (not shown) so as to be opposed to a movable top board of an examination couch 2, on which a subject 3 under examination lies, interposed therebetween and supported to revolve around the body axis of the subject. The quantity of X-rays emitted by X-ray tube 1 and transmitted through subject 3 is detected by X-ray detector 4 and the detected data is supplied to a data acquisition circuit 5. X-ray tube 1 emits a fan-shaped X-ray. X-ray beam detector 4 comprises a large number of detectors (channels) arrayed in a circular arc and provides detected data for each of channels. Circuit 5 converts the detected data to digital data for application to a main controller 9.

Main controller 9 is connected to a system controller 8 which in turn is connected to an X-ray controller 6 and a mechanism controller 7. Various portions of the X-ray scanner are timed by system controller 8. X-ray controller 6 is timed by system controller 8 operating according to instructions from main controller 9 to apply a high voltage to X-ray tube 1, thus generating X-rays. X-ray controller 6 sends a signal, indicating that X-ray tube 1 has emitted X-rays, back to system controller 8. X-ray tube 1, couch 2 and X-ray detector 4 is connected to mechanism controller 7, which can move the gantry and moreover can move the couch top board horizontally while stopping the rotation of the gantry. Mechanism controller 7 counts an amount of shift of top board 2 from its initial position and provides the count to system controller 8. Also connected to main controller 9 are a display section 10 equipped with a CRT display adapted to display images and an input section 11 provided with a keyboard and a trackball.

Figure 2:
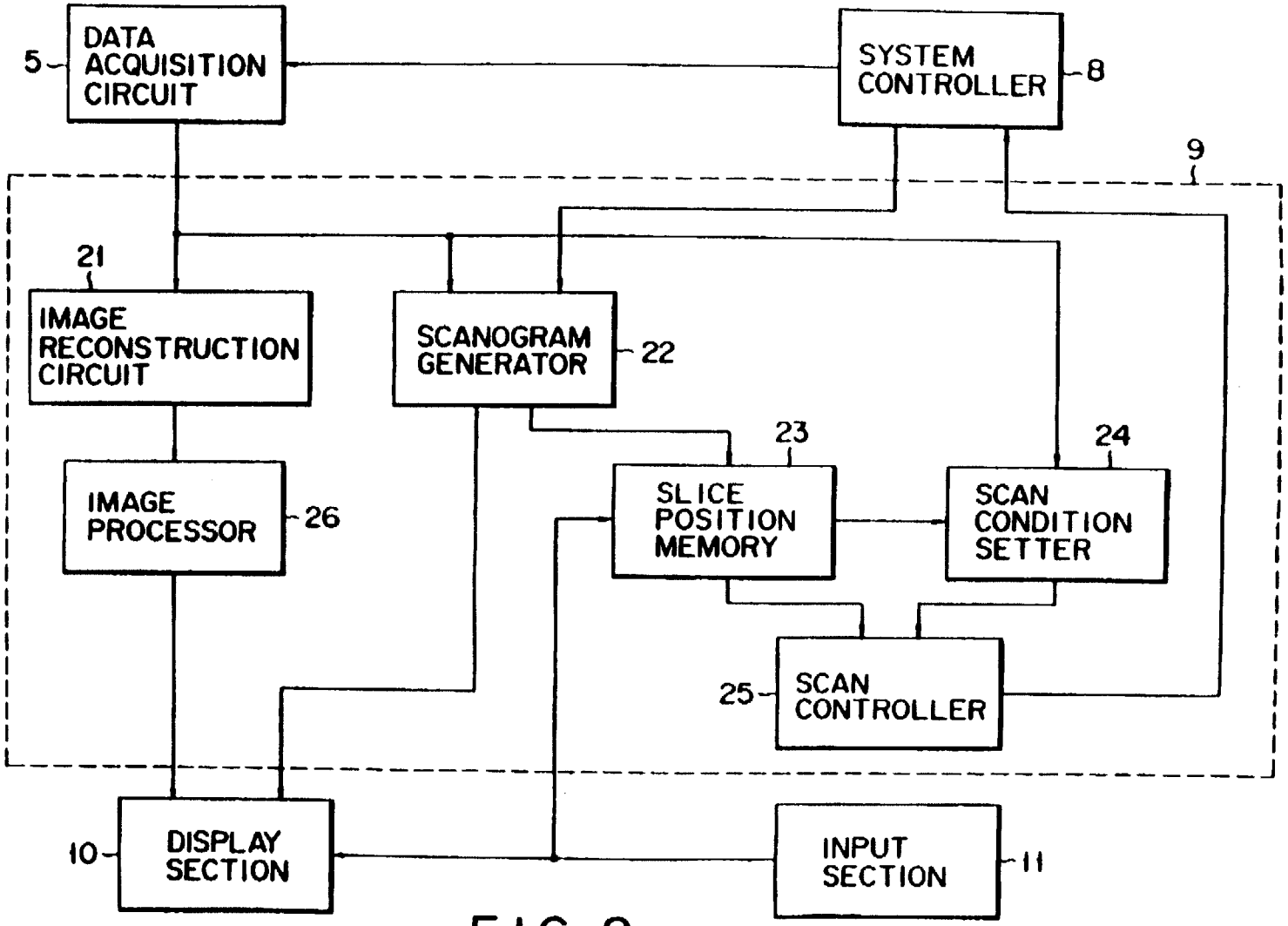
FIG. 2 is a block diagram of the main controller of FIG. 1.

FIG. 2 illustrates a block diagram of main controller 9. Data from data acquisition circuit 5 is entered into an image reconstruction circuit 21, a scanogram generator 22 and a scan condition setter 24. Image reconstruction circuit 21 reconstructs slice images, using, for example a convolution method, from X-ray projection data obtained by directing X-rays to subject 3 with X-ray tube 1 and X-ray detector 4 revolving around the subject. When top board 2 is moved in the direction of the body axis of subject 3 with X-ray tube 1 and X-ray detector 4, which are opposed to each other, fixed to predetermined positions, scanogram generator 22 forms a scanogram of the subject on the basis obtained by passing data of X-rays through the subject 3 in synchronization with the movement of couch 2. The slice images prepared by image reconstruction circuit 21 are applied to an image processor 26 for proper image processing and processed images are then displayed on display section 10. The scanogram prepared by scanogram generator 22 is both displayed on display section 10 and applied to a slice position memory 23. The scanogram is displayed together with a plurality of parallel lines having a pitch specified by input section 11, each of the lines representing a position in which slicing is possible.

A signal specifying a specific slice position is also applied from input section 11 to slice position memory 23 so that only scanogram information associated with the specified slice position is stored in slice position memory 23. The scanogram information is applied from slice position memory 23 to a scan condition setter 24 and a scan controller 25. As a result, scan condition setter 24 determines scan conditions for photographing a slice image in the specified position on the basis of photographic data of the scanogram in the specified position. The determined scan conditions are entered into scan controller 25 so that the photographing of a slice image is carried out. In this way, the scan conditions are set for each of the slice positions.

One of the scan conditions is a tube current for optimizing the quantity of X-rays to allow maximum and minimum values of each channel output of the X-ray detector 4 to fall within a predetermined range. The attenuation of X-rays at subject 3 in the direction of emission of the X-rays (i.e., in the direction in which the scanogram is photographed) can be found from the photographic data of the scanogram. The attenuation of X-rays at the subject in the direction crossing to the above X-ray emission direction can be estimated from an average value of the photographic data of the scanogram for all the channels of X-ray detector 4. If the attenuations of X-rays at the subject can be found for each of the slices in this way, then the optimum quantity of the X-rays will be determined for each of the slices and hence a tube current will be determined.

Next the operation of the embodiment will be described. In general X-ray CT scanners, a scanogram of a subject is photographed prior to photographing of slice images of the subject. The positions of slices of the subject are set on the obtained scanogram and then each of the slices is photographed. Conventionally the scanogram is mainly used only for setting the slice positions along the body axis for the auto index scan. As described above, however, the scanogram is photographed by actually directing X-rays to a subject while the top board on which the subject lies slides with respect to the X-ray tube and the X-ray detector. The optimum scan conditions for photographing slice images can then be determined from the photographic data of the scanogram. For this reason, in the present embodiment, the optimum scan conditions are determined in accordance with photographic data resulting from photographing of a scanogram, and the photographing of slice images is carried out in accordance with the determined scan conditions. According to such automatic setting of the scan conditions, the setting of the optimum scan conditions for each of the slices is made possible irrespective of level of experience of an operator in setting scan conditions, thus alleviating the burden imposed on the operator substantially.

First, subject 3 on the top board is placed before the opening of the gantry not shown, the opening being provided for photographing the subject. Subject 3 is usually placed with the head directed toward the opening of the gantry. Next, the top board 2 on which the subject lies is fed from the base body of the couch to the opening of the gantry. During this period mechanism controller 7 calculates the feed amount of the top board on which the subject lies with the relationship of arrangement between top board 2 of the couch and X-ray tube 1 when top board 2 of the couch is inserted into the photography opening by a predetermined distance taken as the initial condition. The calculated value is fed to scanogram generator 22 of main controller 9 via system controller 8. For example, the feed amount can be represented in terms of the number of revolutions of a stepping motor serving as a driving unit for top board 2 of the couch.

X-ray controller 6 operates X-ray tube 1 to emit fan-shaped X-rays beams at regular intervals in synchronization with the movement of top board 2 of the couch driven by mechanism controller 7 and feeds a signal indicating the emission of X-rays to scanogram generator 22 of main controller 9 via system controller 8. The X-rays emitted by X-ray tube 1 and passed through subject 3 are detected by X-ray detector 4. The X-ray projection data acquired by data acquisition circuit 5 is entered into scanogram generator 22 of main memory 9. Scanogram generator 22 forms a scanogram on the basis of the X-ray projection data, which is sent out to display section 10. Consequently the scanogram of the subject is obtained visually.

The operator observes the scanogram displayed on display section 10 together with the parallel lines of a constant pitch representing the slice-enabling positions and sets a specific slice position or positions through the keyboard not shown. The scanogram information in the position thus set is stored in slice position memory 23.

Scan condition setter 24 determines the optimum tube current for the set slice position which is used later in photographing a corresponding slice image on the basis of the above scanogram projection data (X-ray projection data) and provides the current information to scan controller. 25. The optimum current generates a quantity of X-rays such that the maximum and minimum values of the output of the X-ray detector to fall within a predetermined range.

The execution of photographing slice image is controlled by scan controller 25. That is, X-ray tube 1 and X-ray detector 4 are revolved around the body axis of subject 3 in the slice position, and X-rays are emitted from X-ray tube 1 every time X-ray tube 1 and X-ray detector 4 move a small angular increment that is part of one revolution so that X-ray projection data is acquired by data acquisition section 5. The tube current for each slice position is adjusted to the optimum value by scan controller 25 through X-ray controller 6. The acquired X-ray projection data is entered into image reconstruction circuit 21 so that a slice image is formed. The slice image is displayed on display section 10. Image processor 26 can perform conversion of section or three-dimensional image processing as needed and the resultant image is displayed on display 10.

According to the present embodiment, as described above, the scan conditions for photographing the slice images, specifically the tube current, can automatically be set to the optimum value without the need for setting by the operator and hence the optimum scan conditions (here the tube current) can be set for each of the slice positions irrespective of the level of experience of the operator in setting scan conditions. For this reason, the burden imposed on the operator can be alleviated substantially and moreover slice images can be obtained which are good in visual observation for diagnosis. Furthermore, the photographing time can be shortened as the setting of the scan conditions on a trial and error basis can be avoided.

Figure 3:
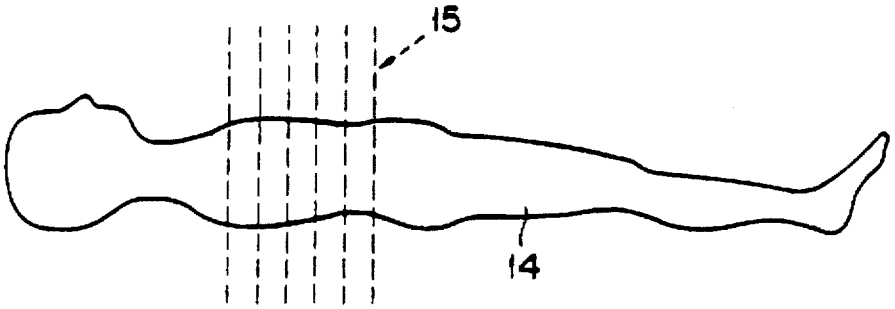
FIG. 3 shows an example of a scanogram.
Figure 4:
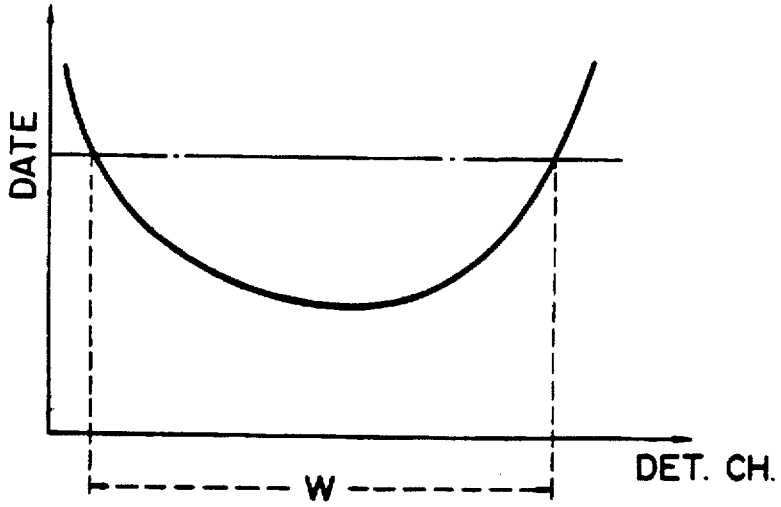
FIG. 4 is a diagram explanatory of an operation for obtaining the optimum values of shifted positions of an X-ray tube and an X-ray detector.

The present invention is not limited to the above embodiment and may be modified in various ways. For example, an X-ray CT scanner, which has a shift function to vary the positions of an X-ray tube and an X-ray detector simultaneously along the line connecting the centers thereof together, is preferably modified to perform automatic setting of shift amounts of the X-ray tube and detector in addition to the automatic setting of the tube current. In this case, the scanogram is photographed from the direction in which the maximum outline of a subject can be found, for example, from the cross direction of the subject so that such a scanogram 14 as shown in FIG. 3 can be obtained. Thus, the maximum outline (the thickness of subject 3 in this case) of the subject can be known. More specifically, by examining the positions of channels of the X-ray detector which have values above a threshold value, or an output value of the X-ray detector obtained when air is scanned, it is possible to find the maximum outline of subject 3 (refer to FIG. 4). If the maximum outline of subject 3 is found, then the shifted position of X-ray tube 1 and X-ray detector 4 can be determined for each of slice positions so that the X-rays passed through subject 3 can be received well by all the channels of detector 4. The determination of the shifted position is also performed by scan condition setter 24. If the shifted position is determined, the shifted position of X-ray tube 1 and X-ray detector 4 will be adjusted to the optimum position for each of the slice positions by scan controller 25 through mechanism controller 7.

With the X-ray CT scanner with a position shift function, it is desired that the automatic setting of the tube current and the automatic setting of the shifted position of X-ray tube 1 and X-ray detector 4 be both performed. However, either of them may be performed, in which case the burden imposed on the operator will be alleviated correspondingly. Furthermore, it is desired that the shifted position be determined first and the tube current be determined next. A tube voltage may be added to the above scan conditions. The scan condition may further include a scan time during which X-ray tube 1 and X-ray detector 4 are rotated around the subject for photographing one slice.

What is claimed is:

1. An X-ray CT scanner comprising:

means for emitting X-rays to a subject under examination;

means for detecting X-rays emitted by said X-ray emitting means and passed through the subject;

scanogram means, coupled to said emitting means and said detecting means, including means for moving said X-ray emitting means with said detecting means along the subject and means for photographing a scanogram of the subject;

means for specifying a slice of the entire photographed scanogram;

determining means, coupled to the scanogram means and specifying means, for determining a scan condition for the slice specified by said slice specifying means based on image information of the scanogram at the slice;

means, coupled to the determining means, for scanning the slice of the subject specified by said specifying means in the scanogram in accordance with the scan condition determined by the determining means, the scanning means including means for rotating the X-ray emitting means and the detecting means around the subject; and means for reconstructing a slice image of the slice of the subject based on the output from the detecting means during scanning by the scanning means.

2. The X-ray CT scanner according to claim 1, in which said determining means includes means for determining a current to be applied to said X-ray emitting means when the slice image is photographed.

3. The X-ray CT scanner according to claim 1, in which said determining means includes means for determining a voltage to be applied to said X-ray emitting means when the slice image is photographed.

4. The X-ray CT scanner according to claim 1, in which said X-ray emitting means includes means for emitting a fan shaped beam, said detecting means includes a plurality of detecting elements arrayed to receive the fan shaped beam each element generating a value corresponding to the amount of energy the element receives from the fan shaped beam, said X-ray emitting means and said detecting means both being mounted on means for allowing positions of said X-ray emitting means and said detecting means to be varied on a line connecting centers thereof, and said determining means includes means for determining positions of said X-ray emitting means and said detecting means at a time of photographing of the slice image.

5. The X-ray CT scanner according to claim 1, in which said scanogram means includes means for displaying the scanogram and a plurality of lines representing slice positions in a superimposed manner; and means for specifying the slice position on the displayed image, and said determining means includes a memory for storing scanogram information for the specified position; and means for determining the scan condition in accordance with the information stored in said memory.

6. The X-ray CT scanner according to claim 2, in which said determining means includes means for determining a current which allows an output level of said detecting means to fall within a predetermined range.

7. The X-ray CT scanner according to claim 3, in which said determining means includes means for determining a voltage which allows an output level of said detecting means to fall within a predetermined range.

8. The X-ray CT scanner according to claim 4, in which said determining means includes means for determining positions of said X-ray emitting means and said detecting means such that the subject is included just within the fan shaped beam from said emitting means.

9. The X-ray CT scanner according to claim 1, in which said determining means includes means for determining a scan time.

10. The X-ray CT scanner according to claim 4, in which the means for determining positions of the X-ray emitting means and the detecting means includes means for determining an outline of the subject at the position in the scanogram corresponding to the slice position.

11. The X-ray CT scanner according to claim 10, in which the means for determining an outline of the subject includes means, coupled to the scanogram means, for determining positions of detecting elements generating a value above a certain threshold.

12. The X-ray CT scanner according to claim 4, in which the determining means includes means for determining a current such that each detecting element will tend to generate a value falling within a predetermined range.

13. The X-ray CT scanner according to claim 12, in which the means for determining a current such that each detecting element will tend to generate a value falling within a predetermined range includes means for determining the attenuation of X-rays by the subject in the direction in which the scanogram is photographed including means for reading the value of each detecting element;

means for determining the attenuation of X-rays by the subject in a direction normal to which the scanogram is photographed including means for averaging the value generated by each detecting element.

14. The X-ray CT scanner according to claim 4, in which the determining means includes means for determining a voltage such that each detecting element will tend to generate a value falling within a predetermined range.

15. The X-ray CT scanner according to claim 14, in which means for determining a voltage such that each detecting element will tend to generate a value falling within a predetermined range includes means for determining the attenuation of X-rays by the subject in the direction in which the scanogram is photographed including means for reading the value of each detecting element;

means for determining the attenuation of X-rays by the subject in a direction normal to which the scanogram is photographed including means for averaging the value generated by each detecting element.

16. The X-ray CT scanner according to claim 5, in which said determining means includes means for determining a current to be applied to said X-ray emitting means when the slice image is photographed.

17. The X-ray CT scanner according to claim 5, in which said determining means includes means for determining a voltage to be applied to said X-ray emitting means when the slice image is photographed.

18. The X-ray CT scanner according to claim 5, in which said determining means includes means for determining a scan time.

19. The X-ray CT scanner according to claim 5, in which said X-ray emitting means includes means for emitting a fan shaped beam, said detecting means includes a plurality of detecting elements arrayed to receive the fan shaped beam each element generating a value corresponding to the amount of energy the element receives from the fan shaped beam, said X-ray emitting means and said detecting means both being mounted on means for allowing positions of said X-ray emitting means and said detecting means to be varied on a line connecting centers thereof, and said determining means includes means for determining positions of said X-ray emitting means and said detecting means at a time of photographing of the slice image.

20. In an X-ray CT scanner having an X-ray emitting means and an X-ray detecting means, a method of operating the X-ray CT scanner to produce a slice image of a subject under examination, comprising the steps, performed by a processor, of:

emitting X-rays from the X-ray emitting means to the subject;

detecting X-rays emitted in the emitting step and passed through the subject;

constructing a scanogram, in response to the emitting step and to the detecting step, including the substeps of moving the X-ray emitting means with the X-ray detecting means along the subject and photographing a scanogram of the subject;

specifying a slice of the entire photographed scanogram;

determining, in response to the step of constructing a scanogram and the step of specifying a slice, a scan condition for the slice specified by the slice specifying step based on image information of the scanogram at the slice;

scanning, in response to the determining step, the slice of the subject specified by the specifying step in the scanogram in accordance with the scan condition determined in the determining step the scanning step including the substep of rotating the X-ray emitting means and the detecting means around the subject; and reconstructing a slice image of the slice of the subject based on the output from the detecting step during scanning in the scanning step.

21. The method according to claim 20, in which the determining step includes the substep of determining a current to be applied to the X-ray emitting means when the slice image is photographed.

22. The method according to claim 20, in which the determining step includes the substep of determining a voltage to be applied to the X-ray emitting means when the slice image is photographed.

23. The method according to claim 20, wherein the detecting means comprises a plurality of detecting elements arrayed to receive a fan shaped beam, the X-ray emitting means and the X-ray detecting means both are mounted on means allowing positions of the X-ray emitting means and the X-ray detecting means to be varied along on a line connecting centers thereof, and in which the X-ray emitting step includes the substep of emitting a fan shaped beam onto the detecting elements, and the detecting step includes the substep of generating a plurality of values each corresponding to the amount of energy each detecting element receives from the fan shaped beam, and the determining step includes the substep of determining positions of the X-ray emitting means and the X-ray detecting means at a time of photographing of the slice image.

24. The method according to claim 20, in which the step of constructing a scanogram includes the substep of displaying the scanogram and a plurality of lines representing slice positions in a superimposed manner; and designating, in response to operator input, the slice position on the displayed image, and the determining step includes the substep of storing scanogram information for the specified position; and determining the scan condition in accordance with the information stored in the memory.

25. The method according to claim 21, in which the determining step includes the substep of determining a current which allows an output level detected in the detecting step to fall within a predetermined range.

26. The method according to claim 22, in which the determining step includes the substep of determining a voltage which allows an output level detected in the detecting step to fall within a predetermined range.

27. The method according to claim 23, in which the substep of determining positions of the X-ray emitting means and the X-ray detecting means includes the substep of determining positions of the X-ray emitting means and the X-ray detecting means such that the subject is included just within the fan shaped beam from the emitting step.

28. The method according to claim 20, in which the determining step includes the substep of determining a scan time.

29. The method according to claim 23, in which the substep of determining positions of the X-ray emitting means and the detecting means includes the substep of determining an outline of the subject at the position in the scanogram corresponding to the slice position.

30. The method according to claim 29, in which the substep of determining an outline of the subject includes the substep of determining, in response to the scanogram step, positions of detecting elements generating a value above a certain threshold.

31. The method according to claim 23, in which the determining step includes the substep of determining a current such that each detecting element will tend to generate a value falling within a predetermined range.

32. The method according to claim 31, in which the substep of determining a current such that each detecting element will tend to generate a value falling within a predetermined range includes the substeps of determining the attenuation of X-rays by the subject in the direction in which the scanogram is photographed including the substep of reading the value of each detecting element;

determining the attenuation of X-rays by the subject in a direction normal to which the scanogram is photographed including the substep of averaging the value generated by each detecting element.

33. The method according to claim 23, in which the determining step includes the substep of determining a voltage such that each detecting element will tend to generate a value falling within a predetermined range.

34. The method according to claim 33, in which the substep of determining a voltage such that each detecting element will tend to generate a value falling within a predetermined range includes the substep of determining the attenuation of X-rays by the subject in the direction in which the scanogram is photographed including the substep of reading the value of each detecting element;

determining the attenuation of X-rays by the subject in a direction normal to which the scanogram is photographed including the substep of averaging the value generated by each detecting element.

35. The method according to claim 24, in which the determining step includes the substep of determining a scan time.

36. The method according to claim 24, wherein the detecting means comprises a plurality of detecting elements arrayed to receive a fan shaped beam, the X-ray emitting means and the X-ray detecting means both are mounted on means allowing positions of the X-ray emitting means and the X-ray detecting means to be varied along on a line connecting centers thereof, and in which the X-ray emitting step includes the substep of emitting a fan shaped beam onto the detecting elements, and the detecting step includes the substep of generating a plurality of values each corresponding to the amount of energy each detecting element receives from the fan shaped beam, and the determining step includes the substep of determining positions of the X-ray emitting means and the X-ray detecting means at a time of photographing of the slice image.

37. The method according to claim 24, in which the determining step includes the substep of determining a current to be applied to the X-ray emitting means when the slice image is photographed.

38. The method according to claim 24, in which the determining step includes the substep of determining a voltage to be applied to the X-ray emitting means when the slice image is photographed.

39. An X-ray CT scanner comprising:

means for emitting X-rays to a subject under examination;

means for detecting X-rays emitted by said X-ray emitting means and passed through the subject;

scanogram means, coupled to said emitting means and said detecting means, including means for moving said X-ray emitting means with said detecting means along the subject and means for photographing a scanogram of the subject, the scanogram containing image information;

determining means, coupled to the scanogram means, for determining a scan condition from image information for a predetermined position in the scanogram including means for determining a scan time;

means for scanning a portion of the subject corresponding to the predetermined position in the scanogram in accordance with the scan condition determined by the determining means including means for rotating the X-ray emitting means and the detecting means around the subject; and means for reconstructing a slice image of the portion of the subject based on the output from the detecting means during scanning by the scanning means.

40. In an X-ray CT scanner having an X-ray emitting means and an X-ray detecting means, a method of operating the X-ray CT scanner to produce a slice image of a subject under examination, comprising the steps of:

emitting X-rays from the X-ray emitting means to the subject;

detecting X-rays emitted in the emitting step and passed through the subject;

constructing a scanogram, in response to the emitting step and to the detecting step, including the substeps of moving the X-ray emitting means with the X-ray detecting means along the subject and photographing a scanogram of the subject, the scanogram containing image information;

determining, in response to the step of constructing a scanogram, a scan condition from image information for a predetermined position in the scanogram including the substep of determining a scan time;

scanning a portion of the subject corresponding to the predetermined position in the scanogram in accordance with the scan condition determined in the determining step including the substep of rotating the X-ray emitting means and the detecting means around the subject; and reconstructing a slice image of the portion of the subject based on the output from the detecting step during scanning in the scanning step.

41. An X-ray CT scanner comprising:

means for emitting X-rays to a subject under examination;

means for detecting X-rays emitted by said X-ray emitting means and passed through the subject;

scanogram means, coupled to said emitting means and said detecting means, including means for moving said X-ray emitting means with said detecting means along the subject and means for photographing a scanogram of the subject;

determining means, coupled to the scanogram means, for determining an operation state of the emitting means including at least one of a current to be applied to the emitting means, a voltage to be applied to the emitting means, and a scan time, the operation state being determined from image information for a predetermined position in the scanogram;

means, coupled to the determining means, for scanning a portion of the subject corresponding to the predetermined position in the scanogram in accordance with the operation state determined by the determining means including means for rotating the X-ray emitting means and the detecting means around the subject; and means for reconstructing a slice image of the portion of the subject based on the output from the detecting means during scanning by the scanning means.

42. In an X-ray CT scanner having an X-ray emitting means and an X-ray detecting means, a method of operating the X-ray CT scanner to produce a slice image of a subject under examination, comprising the steps, performed by a processor, of:

emitting X-rays from the X-ray emitting means to the subject;

detecting X-rays emitted in the emitting step and passed through the subject;

constructing a scanogram, in response to the emitting step and to the detecting step, including the substeps of moving the X-ray emitting means with the X-ray detecting means along the subject and photographing a scanogram of the subject;

specifying a slice of the entire photographed scanogram;

determining, in response to the step of constructing a scanogram and the step of specifying a slice, an operation state of the emitting means including at least one of a current to be applied to the emitting means, a voltage to be applied to the emitting means, and a scan time, the operation state being determined for the slice specified by the slice specifying step based on image information of the scanogram at the slice;

scanning, in response to the determining step, the slice of the subject specified by the specifying step in the scanogram in accordance with the operation state determined in the determining step the scanning step including the substep of rotating the X-ray emitting means and the detecting means around the subject; and reconstructing a slice image of the slice of the subject based on the output from the detecting step during scanning in the scanning step.

*43. An X-ray CT scanner comprising:*

*means for emitting X rays to a subject under examination;*

*means for detecting X rays emitted by said X-ray emitting means and passed through the subject to output X-ray projection data;*

*scanogram means, coupled to said emitting means and said detecting means, including means for moving said X-ray emitting means with said detecting means along the subject, and means for photographing a scanogram of the subject, said means for moving including a board to support said subject which slides relative to said means for emitting and said means for detecting;*

*means for specifying a slice of the entire photographed scanogram corresponding to a slice of the object;*

*determining means, coupled to the scanogram means and specifying means, for determining a scan condition for the slice of the object specified by said slice specifying means based on image information of the scanogram at the specified slice of the scanogram, said image information comprising X-ray projection data;*

*means, coupled to the determining means, for scanning the slice of the subject corresponding to the slice specified in the scanogram by said specifying means in accordance with the scan condition determined by the determining means, the scanning means including means for rotating the X-ray emitting means and the detecting means around the subject; and*

*means for reconstructing a slice image of the subject based on the output from the detecting means during scanning by the scanning means.*

*44. The X-ray CT scanner according to claim 43, in which said determining means includes means for determining a current to be applied to said X-ray emitting means when the slice image is photographed.*

*45. The X-ray CT scanner according to claim 43, in which said determining means includes means for determining a voltage to be applied to said X-ray emitting means when the slice image is photographed.*

*46. The X-ray CT scanner according to claim 43, in which said X-ray emitting means includes means for emitting a fan shaped beam, said detecting means includes a plurality of detecting elements arrayed to receive the fan shaped beam each element generating a value corresponding to the amount of energy the element receives from the fan shaped beam, said X-ray emitting means and said detecting means both being mounted on means for allowing positions of said X-ray emitting means and said detecting means to be varied on a line connecting centers thereof, and said determining means includes means for determining positions of said X-ray emitting means and said detecting means at a time of photographing of the slice image.*

*47. The X-ray CT scanner according to claim 43, in which said scanogram means includes means for displaying the scanogram and a plurality of lines representing slice positions corresponding to slice positions in the object in a superimposed manner; and means for specifying the slice position on the displayed image, and said determining means includes a memory for storing scanogram information for the specified position, the scanogram information including X-ray projection data and slice position; and means for determining the scan condition in accordance with the information stored in said memory.*

*48. The X-ray CT scanner according to claim 44, in which said determining means includes means for determining a current which allows an output level of said detecting means to fall with in a predetermined range.*

*49. The X-ray CT scanner according to claim 45, in which said determining means includes means for determining a*

*voltage which allows an output level of said detecting means to fall within a predetermined range.*

*50. The X-ray CT scanner according to claim 46, in which said determining means includes means for determining positions of said X-ray emitting means and said detecting means such that the subject is included just within the fan shaped beam from said emitting means.*

*51. The X-ray CT scanner according to claim 43, in which said determining means includes means for determining a scan time.*

*52. The X-ray CT scanner according to claim 46, in which the means for determining positions of the X-ray emitting means and the detecting means includes means for determining an outline of the subject at the position in the scanogram corresponding to the slice position.*

*53. The X-ray CT scanner according to claim 52, in which the means for determining an outline of the subject includes means, coupled to the scanogram means, for determining positions of detecting elements generating a value above a certain threshold.*

*54. The X-ray CT scanner according to claim 46, in which the determining means includes means for determining a current such that each detecting element will tend to generate a value falling within a predetermined range.*

*55. The X-ray CT scanner according to claim 54, in which the means for determining a current such that each detecting element will tend to generate a value falling within a predetermined range includes:*

*means for determining the attenuation of X rays by the subject in the direction in which the scanogram is photographed including means for reading the value of each detecting element; and*

*means for determining the attenuation of X rays by the subject in the direction normal to which the scanogram is photographed including means for averaging the value generated by each detecting element.*

*56. The X-ray CT scanner according to claim 46, in which the determining means includes means for determining a voltage such that each detecting element will tend to generate a value falling within a predetermined range.*

*57. The X-ray CT scanner according to claim 56, in which means for determining a voltage such that each detecting element will tend to generate a value falling within a predetermined range includes:*

*means for determining the attenuation of X rays by the subject in the direction in which the scanogram is photographed including means for reading the value of each detecting element; and*

*means for determining the attenuation of X rays by the subject in a direction normal to which the scanogram is photographed including means for averaging the value generated by each detecting element.*

*58. The X-ray CT scanner according to claim 47, in which said determining means includes means for determining a current to be applied to said X-ray emitting means when the slice image is photographed.*

*59. The X-ray CT scanner according to claim 47, in which said determining means includes means for determining a voltage to be applied to said X-ray emitting means when the slice image is photographed.*

*60. The X-ray CT scanner according to claim 47, in which said determining means includes means for determining a scan time.*

*61. The X-ray CT scanner according to claim 47, in which said X-ray emitting means includes means for emitting a fan shaped beam, said detecting means includes a plurality of detecting elements arrayed to receive the fan shaped beam each element generating a value corresponding to the amount of energy the element receives from the fan shaped beam, said X-ray emitting means and said detecting means both being mounted on means for allowing positions of said X-ray emitting means and said detecting means to be varied on a line connecting centers thereof, and said determining means includes means for determining positions of said X-ray emitting means of said detecting means at a time of photographing of the slice image.*

*62. In an X-ray CT scanner having an X-ray emitting means and an X-ray detecting means, a method of operating the X-ray CT scanner to produce a slice image of a subject under examination, comprising the steps, performed by a processor, of:*

*emitting X rays from the X-ray emitting means to the subject;*

*detecting X rays emitted in the emitting step and passed through the subject to output X-ray projection data;*

*constructing a scanogram in response to the emitting step and to the detecting step, including the substeps of*

*moving the subject with respect to the X-ray emitting means and the X-ray detecting means and*

*photographing a scanogram of the subject;*

*specifying a slice of the entire photographed scanogram corresponding to a slice of the object;*

*determining, in response to the step of constructing a scanogram and the step of specifying a slice, a scan condition for the slice of the object specified by the slice specifying by the slice specifying step based on image information of the scanogram at the specified slice of the scanogram, said image information comprising X-ray projection data;*

*scanning, in response to the determining step, the slice of the subject corresponding to the slice specified in the scanogram by the specifying step in accordance with the scan condition determined in the determining step, the scanning step including the substep of*

*rotating the X-ray emitting means and the detecting means around the subject; and*

*reconstructing a slice image of the slice of the subject based on the output from the detecting step during scanning in the scanning step.*

*63. The method according to claim 62, in which the determining step includes the substep of determining a current to be applied to the X-ray emitting means when the slice image is photographed.*

*64. The method according to claim 62, in which the determining step includes the substep of determining a voltage to be applied to the X-ray emitting means when the slice image is photographed.*

*65. The method according to claim 62, wherein the detecting means comprises a plurality of detecting elements arrayed to receive a fan shaped beam, the X-ray emitting means and the X-ray detecting means both are mounted on means allowing positions of the X-ray emitting means and the X-ray detecting means to be varied along on a line connecting centers thereof, and in which the X-ray emitting step includes the substep of:*

*emitting a fan shaped beam onto the detecting elements, and the detecting step includes the substep of*

*generating a plurality of values each corresponding to the amount of energy each detecting element receives from the fan shaped beam,*

*and the determining step includes the substep of determining positions of the X-ray emitting means and the X-ray detecting means at a time of photographing of the slice image.*

*66. The method according to claim 62, in which the step of constructing a scanogram includes the substep of:*

*displaying the scanogram and a plurality of lines representing slice positions corresponding to slice positions in the object in a superimposed manner; and*

*designating, in response to operator input, the slice position on the displayed image, and the determining step includes the substep of*

*storing scanogram information, including X-ray projection data and slice position, for the specified position; and*

*determining the scan condition in accordance with the information stored in the memory.*

*67. The method according to claim 63, in which the determining step includes the substep of determining a current which allows an output level detected in the detecting step to fall within a predetermined range.*

*68. The method according to claim 64, in which the determining step includes the substep of determining a voltage which allows an output level detected in the detecting step to fall within a predetermined range.*

*69. The method according to claim 65, in which the substep of determining positions of the X-ray emitting means and the X-ray detecting means includes the substep of determining positions of the X-ray emitting means and the X-ray detecting means such that the subject is included just within the fan shaped beam from the emitting step.*

*70. The method according to claim 62, in which the determining step includes the substep of determining a scan time.*

*71. The method according to claim 65, in which the substep of determining positions of the X-ray emitting means and the detecting means includes the substep of determining an outline of the subject at the position in the scanogram corresponding to the slice position.*

*72. The method according to claim 71, in which the substep of determining an outline of the subject includes the substep of determining, in response to the scanogram step, positions of detecting elements generating a value above a certain threshold.*

*73. The method according to claim 65, in which the determining step includes the substep of determining a current such that each detecting element will tend to generate a value falling within a predetermined range.*

*74. The method according to claim 73, in which the substep of determining a current such that each detecting element will tend to generate a value falling within a predetermined range includes the steps of:*

*determining the attenuation of X rays by the subject in the direction in which the scanogram is photographed including the substep of reading the value of each detecting element; and*

*determining the attenuation of X rays by the subject in a direction normal to which the scanogram is photographed including the substep of averaging the value generated by each detecting element.*

*75. The method according to claim 65, in which the determining step includes the substep of determining a voltage such that each detecting element will tend to generate a value falling within a predetermined range.*

*76. The method according to claim 75, in which the substep of determining a voltage such that each detecting element will tend to generate a value falling within a predetermined range includes the substeps of:*

*determining the attenuation of X rays by the subject in the direction in which the scanogram is photographed including the substep of reading the value of each detecting element; and*

*determining the attenuation of X rays by the subject in a direction normal to which the scanogram is photographed including the substep of averaging the value generated by each detecting element.*

*77. The method according to claim 66, in which the determining step includes the substep of determining a scan time.*

*78. The method according to claim 66, wherein the detecting means comprises a plurality of detecting elements arrayed to receive a fan shaped beam, the X-ray emitting means and the X-ray detecting means both are mounted on means allowing positions of the X-ray emitting means and the X-ray detecting means to be varied along a line connecting centers thereof, and in which the X-ray emitting step includes the substep of:*

*emitting a fan shaped beam onto the detecting elements, and the detecting step includes the substep of:*

*generating a plurality of values each corresponding to the amount of energy each detecting element receives from the fan shaped beam,*

*and the determining step includes the substeps of:*

*determining positions of the X-ray emitting means and the X-ray detecting means at a time of photographing of the slice image.*

*79. The method according to claim 66, in which the determining step includes the substep of determining a current to be applied to the X-ray emitting means when the slice image is photographed.*

*80. The method according to claim 66, in which the determining step includes the substep of determining a voltage to be applied to the X-ray emitting means when the slice image is photographed.*

*81. An X-ray CT scanner comprising:*

*means for emitting X rays to a subject under examination;*

*means for detecting X rays emitted by said X-ray emitting means and passed through the subject;*

*scanogram means, coupled to said emitting means and said detecting means, including means for moving said X-ray emitting means with said detecting means together with respect to the subject and means for photographing a scanogram of the subject, the scanogram containing image information comprising X-ray projection data, and said means for moving including a board to support said subject which slides relative to said means for emitting and said means for detecting;*

*determining means, coupled to the scanogram means, for determining a scan condition from the X-ray projection data of said image information for a predetermined position in the scanogram corresponding to a slice of the object including means for determining a scan time;*

*means for scanning a portion of the subject corresponding to the predetermined position in the scanogram in accordance with scan condition determined by the determining means, including means for rotating the X-ray emitting means and the detecting means around the subject; and*

*means for reconstructing a slice image of the portion of the subject based on the output from the detecting means during scanning by the scanning means.*

*82. In an X-ray CT scanner having an X-ray emitting means and an X-ray detecting means, a method of operating the X-ray CT scanner to produce a slice image of a subject under examination, comprising the steps of:*

*emitting X rays from the X-ray emitting means to the subject;*

*detecting X rays emitted in the emitting step and passed through the subject;*

*constructing a scanogram in response to the emitting step and to the detecting step, including the substeps of*

*moving the subject with respect to the X-ray emitting means and the X-ray detecting means and*

*photographing a scanogram of the subject, the scanogram containing image information comprising X-ray projection data;*

*determining, in response to the step of constructing a scanogram, a scan condition from the X-ray projection data of the image information for a predetermined position in the scanogram corresponding to the slice of the object, including the substep of determining a scan time;*

*scanning a portion of the subject corresponding to the predetermined position in the scanogram in accordance with the scan condition determined in the determining step including the substep of*

*rotating the X-ray emitting means and the detecting means around the subject; and*

*reconstructing a slice image of the portion of the subject based on the output from the detecting step during scanning in the scanning step.*

*83. An X-ray CT scanner comprising:*

*means for emitting X rays to a subject under examination;*

*means for detecting X rays emitted by said X-ray emitting means and passed through the subject to output X-ray projection data;*

*scanogram means, coupled to said emitting means and said detecting means, including means for moving said X-ray emitting means with said detecting means along the subject and means for photographing a scanogram of the subject, said means for moving including a board to support said subject which slides relative to said means for emitting and said means for detecting;*

*determining means, coupled to the scanogram means, for determining an operation state of the emitting means including at least one of a current to be applied to the emitting means, a voltage to be applied to the emitting means, and a scan time, the operation state being determined from image information for a predetermined position in the scanogram corresponding to a slice of the object, the image information comprising X-ray projection data;*

*means, coupled to the determining means, for scanning a portion of the subject corresponding to the predetermined position in the scanogram in accordance with the operation state determined by the determining means, including means for rotating the X-ray emitting means and the detecting means around the subject; and*

*means for reconstructing a slice image of the portion of the subject based on the output from the detecting means during scanning by the scanning means.*

*84. In an X-ray CT scanner having an X-ray emitting means and an X-ray detecting means, a method of operating the X-ray CT scanner to produce a slice image of a subject under examination, comprising the steps, performed by a processor, of:*

*emitting X rays from the X-ray emitting means to the subject;*

*detecting X rays emitted in the emitting step and passed through the subject to output X-ray projection data;*

*constructing a scanogram, in response to the emitting step and to the detecting step, including the substeps of*

*moving the subject with respect to the X-ray emitting means and the X-ray detecting means and*

*photographing a scanogram of the subject;*

*specifying a slice of the entire photographed scanogram corresponding to a slice of the object;*

*determining, in response to the step of constructing a scanogram and the step of specifying a slice, an operation state of the emitting means including at least one of a current to be applied to the emitting means, a voltage to be applied to the emitting means, and a scan time, the operation state being determined for the slice of the object corresponding to the slice specified by the slice specifying step based on image information of the scanogram at the specified slice of the scanogram, the image information comprising X-ray projection data;*

*scanning, in response to the determining step, the slice of the subject corresponding to the slice specified in the scanogram by the specifying step in accordance with the operation state determined in the determining step, the scanning step including the substep of*

*rotating the X-ray emitting means and the detecting means around the subject; and*

*reconstructing a slice image of the slice of the subject based on the output from the detecting step during scanning in the scanning step.*

* * * * *